US010048280B2

(12) United States Patent
Struck

(10) Patent No.: US 10,048,280 B2
(45) Date of Patent: Aug. 14, 2018

(54) IMMUNOASSAY FOR THE DETECTION OF PROCALCITONIN

(71) Applicant: B.R.A.H.M.S GMBH, Henningsdorf (DE)

(72) Inventor: Joachim Struck, Berlin (DE)

(73) Assignee: B.R.A.H.M.S GMBH, Hennigsdorf (DE)

( * ) Notice: Subject to any disclaimer, the term of this patent is extended or adjusted under 35 U.S.C. 154(b) by 0 days.

(21) Appl. No.: 15/412,648

(22) Filed: Jan. 23, 2017

(65) Prior Publication Data

US 2017/0131297 A1 May 11, 2017

Related U.S. Application Data

(63) Continuation of application No. 13/266,594, filed as application No. PCT/EP2010/055648 on Apr. 27, 2010, now abandoned.

(30) Foreign Application Priority Data

Apr. 28, 2009 (EP) .................................... 09158983
Jul. 10, 2009 (EP) .................................... 09165227

(51) Int. Cl.
  *G01N 33/74* (2006.01)
  *C07K 16/26* (2006.01)
  *C12N 5/16* (2006.01)

(52) U.S. Cl.
  CPC ............. *G01N 33/74* (2013.01); *C07K 16/26* (2013.01); *C12N 5/16* (2013.01); *C07K 2317/34* (2013.01); *G01N 2333/5753* (2013.01)

(58) Field of Classification Search
  None
  See application file for complete search history.

(56) References Cited

U.S. PATENT DOCUMENTS

| 4,208,479 | A | 6/1980 | Zuk et al. |
| 5,639,617 | A | 6/1997 | Bohuon |
| 2007/0037158 | A1 | 2/2007 | Gardiner et al. |

OTHER PUBLICATIONS

HyTest DataSheet for Catalog No. 4C10, Monoclonal mouse anti-human calcitonin; downloaded from https://shop.hytest.fi/product/calcitonin-human-antibody [retrieved Aug. 16, 2015], (Two Pages).
HyTest DataSheet for Catalog No. 4PC47, Monoclonal mouse anti-human procalcitonin (PCT); downloaded from https://shop.hytest.fi/product/procalcitonin-human-antibody [retrieved Aug. 16, 2015], (One Page).
Kuby et al., Immunology, W.H. Freeman and Company, (1992), p. 125.
Bost et al., Immunol., Invest., vol. 17, (1988), pp. 577-586.
Bendayan J. Histochem. Cytochem., vol. 43, (1995), pp. 881-886.
Morgenthaler et al., "Production of procalcitonin (PCT) in non-thyroidal tissue after LPS injection", Horm Metab Res. (May 2003), vol. 35(5), pp. 290-295.
Becker et al., Procalcitonin in sepsis and systemic inflammation: a harmful biomarker and a therapeutic targetbph_433 253; British Journal of Pharmacology (2010), vol. 159, pp. 253-264.
Kremmer et al., "A new strategy for the development of monoclonal antibodies for the determination of human procalcitonin in serum samples" Anal Bioanal Chem (2012), vol. 402, pp. 989-995.
Wrenger et al., "Amino-terminal truncation of procalcitonin, a marker for systemic bacterial infections, by dipeptidyl peptidase IV (DP IV)" FEBS Letters, vol. 466, (2000), pp. 155-159.
Harlow et al., "Antibodies: A Laboratory Manual", (1988), Cold Spring Harbor Laboratory Press., Cold Spring Harbor, NY, pp. 23-24, 59-76.
Wolfe, S.L., Molecular and Cellular Biology, (1993), pp. 790-793.
Conlon et al., "Structural characterization of a high-molecular-mass form of calcitonin [procalcitonin-(60-116)-peptide] and its corresponding N-terminal flanking peptide [procalcitonin-(1-57)-peptide] in a human medullary thyroid carcinoma", Biochem. J. (1988), vol. 256, pp. 245-250.
Kumar, "Predicting Antigenic Peptides", (Sep. 24, 2008), retrieved from http://bioinformatictools.blogspot.com/2008/09/predicting-antigenic-peptides.html on May 26, 2015, one page.
Predicted Antigenic Peptides, http://imed.med.ucm.es/Tools/antigenic.pl, results obtained by the examiner on May 20, 2015 using PCT sequence (two pages total).
Meisner et al., "Induction of procalcitonin and proinflammatory cytokines in an anhepatic baboon endotoxin shock model" Shock, (Feb. 2003), vol. 19(2), pp. 187-190.
Amendments to the claims of EP10715266.2 submitted in the EPO on Nov. 21, 2014. (10 pages total).
International Search Report of PCT/EP2010/055648 (dated May 28, 2010).

(Continued)

*Primary Examiner* — Christine Foster
(74) *Attorney, Agent, or Firm* — Millen White Zelano & Branigan, PC

(57) ABSTRACT

The present invention relates to an in vitro method for the detection of Procalcitonin or a fragment thereof of at least 20 amino acid residues in length in a biological sample derived from a bodily fluid obtained from a subject, comprising the steps of: (i) contacting said sample with at least two antibodies or functional fragments thereof directed against different epitopes within Procalcitonin, and (ii) qualitatively or quantitatively detecting binding of said at least two antibodies to Procalcitonin or said fragment thereof, wherein binding indicates the presence or concentration of Procalcitonin or said fragment in said sample, wherein at least one antibody or functional fragment thereof is directed against an epitope comprised in the sequence spanning amino acid residues 2 to 52 of Procalcitonin. The invention also pertains to antibodies directed against an N-terminal epitope of Procalcitonin and kits comprising antibodies directed against PCT.

9 Claims, 5 Drawing Sheets

(56) References Cited

OTHER PUBLICATIONS

Hytest: "Hytest News—Procalcitonin" [Online] Feb. 2008, pp. 1-8, XP002584672, Product Data Sheet Retrieved from the Internet: URL:http://www.hytest.fi/data_sheets/newsletters/Procalcitonin %20Newsletter.pdf.
P.M. Kramer et al., "Development and Characterization of New Rat Monoclonal Antibodies for Procalcitonin", Analytical and Bioanalytical Chemistry, vol. 392, No. 4 (Oct. 2008) pp. 727-736.
H. Yamada et al., "Determination of Procalcitonin Concentration Using the SphereLight 180 Clinical Auto-Analyzer", Clinica Chimica Acta, vol. 388, No. 1-2 (Feb. 2008) pp. 38-40.
PCT International Prelim. Report on Patentability & Written Opin. dated Nov. 1, 2011 (7 pp.).
Brahms Response to Written Opinion dated Jun. 6, 2012, PCT/EP2010/055648 (15 pp.).
Order List for Hy Test's PCT monoclonal antibodies filled 2004-2008 (customer names redacted) (8 pp.).
HyTest General Product Cat., Aug. 2007 (3 pp.).
HyTest General Product Cat., Jul. 2006 (3 pp.).
HyTest General Product Cat., Jun. 2005 (3 pp.).
HyTest Cardiac Markers Cat., 2004 (5 pp.).
Exhibit 3—Dr. Vladimir Filatov's Declaration dated Jul. 28, 2015 with translation, 6 pages total.
Exhibit 4—Exhibit Reineke, U., Methods in Molecular Biology, vol. 524 with translation, doi: 10.1007/978-1-59745-450-6_14, pp. 203-211.
Exhibit 5—Dictionary of Molecular and Cellular Biology, Tokyo Kagaku Douzin with translation, (one page).
Exhibit 6—Petition dated Dec. 17, 2015 in connection with JP Patent 6009938 with translation, (four pages).
Exhibit 7—Examination Guidelines, Part III, Chapter 2, Section 3, 3.1.1. with translation, (one page).
Exhibit 8—Examination Guidelines, Part III, Chapter 2, Section 3, 3.1.4 with translation, (one page).
Exhibit 13—Third Party Observation dated Aug. 5, 2014 in connection with EP10715266.2, (7 pages).
Exhibit 14—Third Party Observation dated Aug. 12, 2016 in connection with EP10715266.2, (7 pages total).
Exhibit 15—Further Proceeding dated Sep. 26, 2016 in connection with EP10715266.2, (9 pages total).
The Notice of Reasons for Revocation in connection with Opposition No. 2017-700370 (JP Patent No. 6009938), Exhibit A16, dated Jun. 9, 2017, 16 pages.
Exhibit 2—Dr. Vladimir Filatov's Declaration dated Aug. 11, 2016 with translation, (four pages).
Notification of Opposition filed in corresponding Japan application 2015-062973 dated Oct. 17, 2017 which list of exhibits 1-16 cited in the opposition brief, (two pages).
Office Action in corresponding Chinese application 201080016842.6 dated Feb. 28, 2018 with citations, with 3-page translation filed Apr. 17, 2018.
Jemmerson, R., and Paterson, Y.; Mapping antigenic sites on proteins: implications for the design of synthetic vaccines.; 1986) BioTechniques 4, 18-31.
Geysen: Journal of Immunological Methods [Sep. 1, 1987, 102(2):259-274] Abstract.
Morris: Epitope Mapping Protocols: Methods in Molecular Biology, vol. 66: ISBN-10 0-89603-375-9 ISBN-13 978-0-89603-375-7 pp. 149-169 and TOC.
Logan: Epitope mapping of the alpha-toxin of Clostridium perfringens.: Infect Immun. Dec. 1991;59(12):4338-42.
Mathiesen: Analysis of a subclass-restricted HIV-1 gp41 epitope by omission peptides. Immunology. May 1989;67(1):1-7.
Hytest General Product Catalog 2005-2006 (11 pages) Author: Anonymous, "D3".
HyTest TechNotes Procalcitonin (8 pages) Year : unknown Author: Anonymous, (Dated Jun. 2014).
Zhang: Approaches for Antigan Epitope Study and the Development of Antigen Epitioes for Foot and Mouth Discease Virus; Microbiology; Aug. 2008 35(8) 1302-1310 (Englsih Abstract).
Haixia: Progress in Microbiology Immunology, 2007, vol. 35, Issue 1, pp. 54-58 (English Abstract).
Deng et al. "Identification of VP3 Antigenic Epitopes of Infectious Bursal Disease Virus" Chinese Journal of Virology Jul. 2007 vol. 74 No. 4 pp. 305-310, (accompanying English abstract).
Deng: Identification of VP3 Antigenic Epitopes of Infectious Bursal Disease Virus (Abstract) (2007) pp. 311, Chinese Journal of Virology, vol. 23, Issue 4.
Jun: Science in China Series C: Life Sciences, 2006, vol. 36, Issue 5, pp. 346-354 (English Abstract), (English abstract filed Apr. 17, 2013).

Fig. 5

```
SEQ ID NO:1

1    APFRSALESS PADPATLSED EARLLLAALV QDYVQMKASE LEQEQEREGS
51   SLDSPRSKRC GNLSTCMLGT YTQDFNKFHT FPQTAIGVGA PGKKRDMSSD
101  LERDHRPHVS MPQNAN
```

IMMUNOASSAY FOR THE DETECTION OF PROCALCITONIN

SEQUENCE LISTING

The instant application contains a Sequence Listing which has been submitted electronically in ASCII format and is hereby incorporated by reference in its entirety. Said ASCII copy, created on Jun. 26, 2017, is named SIMANDI-0012-C01_SL.txt and is 18,192 bytes in size.

FIELD OF THE INVENTION

The present invention is in the field of clinical diagnostics. Particularly the present invention relates to the determination of the level of Procalcitonin (PCT) in a sample derived from a bodily fluid of a subject.

BACKGROUND OF THE INVENTION

Procalcitonin (PCT) is known as a biomarker, that reflects the presence and severity of local and systemic bacterial infections, i.e. sepsis (Assicot et al., Lancet 1993; 341:515-8; Muller et al., Crit Care Med 2000; 28:977-83; Harbarth et al., Am J Respir Crit Care Med 2001; 164:396-402; Becker et al., Crit Care Med 2008; 36:941-52; Becker et al, J Clin Endocrinol Metab 2004; 89:1512-25; Nobre et al., Am J Respir Crit Care Med 2008; 177:498-505; Christ-Crain et al., Lancet 2004; 363:600-7; Stolz et al., Chest 2007; 131: 9-19; Christ-Crain et al, Am J Respir Crit Care Med 2006; 174:84-93; Briel et al., Arch Intern Med 2008; 168:2000-7; discussion 7-8).

Antigen-specific antibodies are a key tool for the development of immunoassays. Several antibodies against PCT-derived peptides have been described, which have been used in immunoassays to detect PCT, but only few have been tested for their use in sandwich immunoassays to detect native PCT (Table 1). Sandwich immunoassays employing antibodies against the calcitonin- and katacalcin moieties of PCT have been developed to measure PCT in human samples on a routine basis.

For conditions associated with elevated PCT concentrations (excluding medullary thyroid carcinoma), especially bacterial infections and sepsis, it is believed that not only full-length PCT (ca. 13 kDa), but also PCT-derived fragments are present in the blood circulation of patients. Particularly, proteolytic cleavage just upstream from the calcitonin moiety of PCT has been discussed to occur (Muller, et al. Crit Care Med 2000; 28:977-83; Whang et al., J Clin Endocrinol Metab 1998; 83:3296-301), which would lead to two fragments (both ca. 6-7 kDa). However, experimental evidence on this is sparse: Circulating PCT has been isolated from sepsis patients by affinity chromatography using an antibody directed against the calcitonin moiety of PCT, and it has been concluded that PCT3-116 is the major circulating PCT species (Weglohner et al., Peptides 2001; 22:2099-103.). However, several selection steps were performed in this analysis, i.e. only peptides with a calcitonin-containing epitope were purified, and not all relevant fractions from the subsequent reversed-phase HPLC were analyzed Immunoassays for PCT also have not been suitable to address the question of PCT-fragmentation, because either competitive assays involving a single antibody were used (Whang, et al. J Clin Endocrinol Metab 1998; 83:3296-301), or sandwich immunoassays involving two antibodies with epitopes located closely to each other in the C-terminal half of PCT and not covering a broad moiety of PCT were used (Morgenthaler et al., Clin Chem 2002; 48:788-90).

Antibodies against the very N-terminus of PCT have been used in conjunction with an antibody against the katacalcin moiety of PCT in a sandwich assay to detect in samples of septic patients PCT species with an intact N-terminus (DE 10 2007 009 751). N-terminally intact PCT species were found to have different in vivo kinetics than PCT immunoreactivity which was detected with a sandwich immunoassay employing antibodies against the calcitonin- and katacalcin moieties of PCT. Additionally, these N-terminally intact PCT species were found to make up only ca. 10-20% of PCT immunoreactivity which was detected with a sandwich immunoassay employing antibodies against the calcitonin- and katacalcin moieties of PCT. It is not clear, however, at which site(s) between the very N-terminus of PCT and the calcitonin moiety proteolytic cleavage(s) occur(s), which lead(s) to the different concentrations of analytes observed. While it can be assumed that PCT1-116 is cleaved N-terminally by the action of DPP IV leading to PCT3-116 (Weglohner, et al. Peptides 2001; 22:2099-103; Wrenger et al., FEBS Lett 2000; 466:155-9), it is unclear, whether additionally or alternatively PCT1-116 can be cleaved at another site in the middle of the molecule.

Thus, it is unclear, whether an antibody having an epitope roughly upstream from the calcitonin moiety (precisely: upstream from position 53) of PCT, which does not include the very N-terminus of PCT (i.e. position 1 of PCT1-116), in conjunction with an antibody having another epitope, for example an epitope downstream from position 53 (as for instance an epitope within the calcitonin- or katacalcin moiety of PCT), can be used in a sandwich immunoassay to detect native PCT in a patient sample comparably as a sandwich immunoassay employing antibodies having an epitope within the calcitonin moiety of PCT and an antibody with an epitope downstream of that, as for instance an antibody with an epitope within the katacalcin moiety of PCT. Such sandwich immunoassay has been recently described using recombinant PCT as analyte, but recovery of native PCT from patient samples has not been evaluated, and the potential issue of PCT fragmentation has not even been discussed our speculated about (Kramer et al., Anal Bioanal Chem 2008; 392:727-36).

The present invention is partially based on the surprising finding of the inventors that antibodies directed against epitopes contained in amino acid positions 2-52 of Procalcitonin are suitable for measuring PCT using sandwich immunoassays, since PCT is not cleaved in the middle of the molecule.

DESCRIPTION OF THE INVENTION

The present invention provides for an improved assay for the determination of PCT levels in samples of bodily fluids based on a novel combination of antibodies directed to PCT.

Thus, the present invention relates to an in vitro method for the detection of Procalcitonin or a fragment thereof of at least 20 amino acid residues in length in a biological sample derived from a bodily fluid obtained from a subject, comprising the steps of:
  a. contacting said sample with at least two antibodies or functional fragments thereof directed against different epitopes within Procalcitonin,
  b. qualitatively or quantitatively detecting binding of said at least two antibodies to Procalcitonin or said fragment thereof, wherein binding indicates the presence or concentration of Procalcitonin or said fragment in said sample, wherein at least one antibody or functional fragment thereof is directed against an epitope comprised in the sequence spanning amino acid residues 2 to 52 of Procalcitonin.

In the context of the present invention, the antibody or functional fragment thereof, which is directed against an epitope comprised in the sequence spanning amino acid residues 2 to 52 of Procalcitonin, is a polyclonal or a monoclonal antibody.

It is preferred in the context of the present invention that the antibody or functional fragment thereof, which is directed against an epitope comprised in the sequence spanning amino acid residues 2 to 52 of Procalcitonin, is a monoclonal antibody.

Preferably the other antibody or functional fragment thereof is directed against an epitope comprised in the sequence spanning amino acid residues 53 to 116 of Procalcitonin.

The at least two antibodies employed in the methods of the present invention preferably do not exhibit significant (that is >10%) cross-reactivities to the epitopes of the respective other antibody or antibodies. An antibody directed against an epitope in the sequence spanning amino acid residues 2 to 52 of Procalcitonin is specific for this epitope and exhibits thus no significant cross-reactivity with an epitope in the sequence spanning amino acid residues 53 to 116 of Procalcitonin and vice versa. Hence, the antibodies of the present invention are specific for their epitope in PCT and show no significant cross-reactivity with other epitopes, particularly non-overlapping epitopes in this peptide.

Preferably herein, the epitope comprised in the sequence spanning amino acid residues 2 to 52 of Procalcitonin is an epitope comprised in the sequence spanning amino acid residues 16 to 40 of Procalcitonin. More preferably, the epitope comprised in the sequence spanning amino acid residues 16 to 40 of Procalcitonin is selected from a group consisting of an epitope comprised in the sequence spanning amino acid residues 21 to 40 of Procalcitonin, an epitope comprised in the sequence spanning amino acid residues 16 to 35 of Procalcitonin and an epitope comprised in the sequence spanning amino acid residues 25 to 37 of Procalcitonin.

The epitope comprised in the sequence spanning amino acid residues 53 to 116 of Procalcitonin is preferably an epitope comprised in the sequence spanning amino acid residues 96 to 116 of Procalcitonin or an epitope comprised in the sequence spanning amino acid residues 60 to 91 of Procalcitonin.

In a particular embodiment of the method of the present invention, the concentration of Procalcitonin or a fragment thereof in the sample is quantified.

Preferably, the subject according to the present invention is a human or non-human animal, preferably a mammal, most preferably the subject is a human.

In the context of the present invention, the antibody or functional fragment thereof, which is directed against an epitope comprised in the sequence spanning amino acid residues 53 to 116 of Procalcitonin, is a polyclonal or a monoclonal antibody. Preferably, the antibody or functional fragment thereof, which is directed against an epitope comprised in the sequence spanning amino acid residues 53 to 116 of Procalcitonin, is a monoclonal antibody.

The antibody or functional fragment thereof, which is directed against an epitope comprised in the sequence spanning amino acid residues 2 to 52 of Procalcitonin, is preferably an IgG or is derived from IgG. Similarly, the antibody or functional fragment thereof, which is directed against an epitope comprised in the sequence spanning amino acid residues 53 to 116 of Procalcitonin, is preferably an IgG or is derived from IgG.

The bodily fluid in the context of the method of the present invention is preferably selected from the group of blood, serum, plasma, cerebrospinal fluid, urine, saliva, sputum, and pleural effusions.

In a preferred embodiment of the method of the present invention, at least one of the at least two antibodies or functional fragments thereof is immobilized on a solid surface. More preferably, one of the at least two antibodies or functional fragments thereof is immobilized on a solid surface. It is preferred, that at least one of the other antibody or antibodies is labelled, preferably by covalent attachment of a chemiluminescent or fluorescent dye.

In a particular embodiment of the method, the antibody or functional fragment thereof that is directed against an epitope comprised in the sequence spanning amino acid residues 2 to 52 of Procalcitonin is immobilized on a solid surface. In another particular embodiment, the antibody or functional fragment thereof that is directed against an epitope comprised in the sequence spanning amino acid residues 53 to 116 of Procalcitonin is immobilized on a solid surface.

The present invention also pertains to an antibody or a functional fragment thereof directed against an epitope comprised in the sequence spanning amino acid residues 16 to 40 of Procalcitonin.

Preferably, the antibody or functional fragment thereof is directed against an epitope is selected from a group consisting of an epitope comprised in the sequence spanning amino acid residues 21 to 40 of Procalcitonin, an epitope comprised in the sequence spanning amino acid residues 16 to 35 of Procalcitonin and an epitope comprised in the sequence spanning amino acid residues 25 to 37 of Procalcitonin. It is preferred that the antibody is monoclonal.

The antibody of the present invention may preferably be produced by genetic immunization.

Briefly, monoclonal antibodies against PCT can be generated by genetic immunization, e.g. principally following the procedure set out in Costagliola et al., J Immunol 1998; 160:1458-65. The PCT coding sequence can be cloned by standard procedures into a vector. Animal, e.g. mice, can then be injected with said vector. Injections may be repeated after e.g. 3 and 6 weeks. The animals are sacrificed e.g. after 18 weeks. Spleen cells of the sacrificed animals are then fused with SP2/0 myeloma cells to generate hybridoma cell lines which are then screened for their ability to secrete antibodies that would bind to immobilized recombinant human PCT.

The monoclonal antibody directed against an epitope comprised in the sequence spanning amino acid residues 16 to 40 of Procalcitonin according to the present invention may preferably be produced by a hybridoma cell line that is deposited at the DSMZ, Deutsche Sammlung von Mikroorganismen und Zellkulturen GmbH (DSMZ), Inhoffenstr. 7 B D-3 8124 Braunschweig Germany, under accession number DSM ACC2993 or DSM ACC2996 or DSM ACC2997. These cell lines produce particular monoclonal antibodies directed against an epitope comprised in the sequence spanning amino acid residues 16 to 40 of Procalcitonin according to the invention. The hybridoma cell line producing monoclonal antibody FX7A7 has been deposited at the Deutsche Sammlung von Mikroorganismen und Zellkulturen GmbH (DSMZ) on Jun. 4, 2009 under accession number DSM ACC2997. The hybridoma cell line producing monoclonal antibody FW5H6 has been deposited at the Deutsche Sammlung von Mikroorganismen und Zellkulturen GmbH (DSMZ) on Jun. 4, 2009 under accession number DSM ACC2996. The hybridoma cell line producing monoclonal antibody FX1G5 has been deposited at the Deutsche Sammlung von Mikroorganismen und Zellkulturen GmbH (DSMZ) on Apr. 29, 2009 under accession number DSM ACC2993. All hybridoma cell lines have been produced according to the principles described herein above and in more detail in Example 1.

In a further aspect, the present invention relates to a kit at least comprising
 a. a first antibody or a functional fragment thereof directed against an epitope comprised in the sequence spanning amino acid residues 2 to 52 of Procalcitonin, and
 b. a second antibody or a functional fragment thereof directed against an epitope comprised in the sequence spanning amino acid residues 53 to 116 of Procalcitonin.

Preferably, the first antibody of the kit is directed against an epitope comprised in the sequence spanning amino acid residues 16 to 40 of Procalcitonin, preferably against an epitope that is selected from a group consisting of an epitope comprised in the sequence spanning amino acid residues 21 to 40 of Procalcitonin, an epitope comprised in the sequence spanning amino acid residues 16 to 35 of Procalcitonin and an epitope comprised in the sequence spanning amino acid residues 25 to 37 of Procalcitonin.

It is preferred that the first antibody is a monoclonal antibody. It is also preferred that the second antibody is a monoclonal antibody.

In a preferred embodiment of the kit, the second antibody is directed against an epitope comprised in the sequence spanning amino acid residues 60 to 91 of Procalcitonin or directed against an epitope comprised in the sequence spanning amino acid residues 96 to 116 of Procalcitonin.

The invention further relates to the use of a kit according to the present invention in a sandwich immunoassay format for the detection and or quantification of Procalcitonin or a fragment thereof in a biological sample from a bodily fluid. Such a fragment at least comprises a sequence spanning the two epitopes against which the two antibodies are directed.

Furthermore, the present invention relates to the use of the method according to the present invention, the antibody according to the present invention or the kit according to the present invention for the determination of the presence or absence of Procalcitonin or a fragment thereof or for the quantification of Procalcitonin or a fragment thereof in a biological sample from a bodily fluid.

Preferably, the method, antibody and kit are used for the diagnosis, prognosis, risk stratification, therapy monitoring, therapy guidance, or stratification for application of therapeutic measures of a disease or condition associated with elevated procalcitonin levels.

The disease or condition is preferably selected from the group of local bacterial infections (particularly in the airways and the lung), sepsis, severe sepsis, septic shock. The disease or condition may also be selected from the group of non-infectious diseases including but not restricted to cardiovascular diseases (acute coronary syndrome, heart failure, coronary artery disease, atherosclerosis, stroke), cancer, diabetes, chronic gastrointestinal diseases, chronic renal diseases, hypertension, orthopaedic diseases including osteoporosis, and neurodegenerative diseases including Alzheimer's disease. All diseases or conditions mentioned above might or might not be associated with one or more co-morbidities.

The antibodies of the present invention have preferably affinities for their respective epitopes in the range of from $10^8$ to $10^{11}$ $M^{-1}$, preferably above $10^9 M^{-1}$.

The term "antibody" generally comprises monoclonal and polyclonal antibodies and binding fragments thereof, in particular Fc-fragments as well as so called "single-chain-antibodies" (Bird R. E. et al. (1988) Science 242:423-6), chimeric, humanized, in particular CDR-grafted antibodies, and dia or tetrabodies (Holliger P. et al. (1993) Proc. Natl. Acad. Sci. U.S.A. 90:6444-8). Also comprised are immunoglobulin like proteins that are selected through techniques including, for example, phage display to specifically bind to the molecule of interest contained in a sample. In this context the term "specific binding" refers to antibodies raised against the molecule of interest or a fragment thereof. An antibody is considered to be specific, if its affinity towards the molecule of interest or the aforementioned fragment thereof is at least preferably 50-fold higher, more preferably 100-fold higher, most preferably at least 1000-fold higher than towards other molecules comprised in a sample containing the molecule of interest. It is well known in the art how to make antibodies and to select antibodies with a given specificity. As stated herein above, monoclonal antibodies are preferred.

The preferred assays and detection methods according to the present invention comprise immunoassays in various formats such as for instance radioimmunoassay (RIA), chemiluminescence- and fluorescence-immunoassays, Enzyme-linked immunoassays (ELISA), Luminex-based bead arrays, protein microarray assays, and rapid test formats such as for instance immunochromatographic strip tests.

The assays can be homogenous or heterogeneous assays, competitive and non-competitive sandwich assays. In a particularly preferred embodiment employing the two antibodies according to the present invention, the assay is in the form of a sandwich assay, which is a non-competitive immunoassay, wherein PCT or a fragment thereof to be detected and/or quantified is bound to the first antibody and to the second antibody. The first antibody may be bound to a solid phase, e.g. a bead, a surface of a well or other container, a chip or a strip, and the second antibody is an antibody which is labeled, e.g. with a dye, with a radioisotope, or a reactive or catalytically active moiety. The amount of labeled antibody bound to the analyte is then measured by an appropriate method. The general composition and procedures involved with "sandwich assays" are well-established and known to the skilled person. (*The Immunoassay Handbook*, Ed. David Wild, Elsevier LTD, Oxford; 3rd ed. (May 2005), *ISBN*-13: 978-0080445267; Hultschig C et al., *Curr Opin Chem Biol.* 2006 February; 10(1):4-10. PMID: 16376134), incorporated herein by reference).

In a particularly preferred embodiment the assay comprises the two antibodies according to the present invention which are both present as dispersions in a liquid reaction mixture, wherein a first labeling component is attached to the first antibody, wherein said first labeling component is part of a labeling system based on fluorescence- or chemiluminescence-quenching or amplification, and a second labeling component of said marking system is attached to the second antibody, so that upon binding of both antibodies to the analyte a measurable signal is generated that allows for the detection of the formed sandwich complexes in the solution comprising the sample.

Even more preferred, said labeling system comprises rare earth cryptates or rare earth chelates in combination with a fluorescence dye or chemiluminescence dye, in particular a dye of the cyanine type.

In the context of the present invention, fluorescence based assays comprise the use of dyes, which may for instance be selected from the group comprising FAM (5- or 6-carboxyfluorescein), VIC, NED, Fluorescein, Fluoresceinisothiocyanate (FITC), IRD-700/800, Cyanine dyes, such as CY3, CY5, CY3.5, CY5.5, Cy7, Xanthen, 6-Carboxy-2',4',7',4,7-hexachlorofluorescein (HEX), TET, 6-Carboxy-4',5'-dichloro-2',7'-dimethodyfluorescein (JOE), N,N,N',N'-Tetramethyl-6-carboxyrhodamine (TAMRA), 6-Carboxy-X-rhodamine (ROX), 5-Carboxyrhodamine-6G (R6G5), 6-carboxyrhodamine-6G (RG6), Rhodamine, Rhodamine Green, Rhodamine Red, Rhodamine 110, BODIPY dyes, such as BODIPY TMR, Oregon Green, Coumarines such as Umbelliferone, Benzimides, such as Hoechst 33258; Phenanthridines, such as TEXAS RED, YAKIMA YELLOW, ALEXA FLUOR, PET, Ethidiumbromide, Acridinium dyes, Carbazol dyes, Phenoxazine dyes, Porphyrine dyes, Polymethin dyes, and the like.

In the context of the present invention, chemiluminescence based assays comprise the use of dyes, based on the physical principles described for chemiluminescent materials in Kirk-Othmer, Encyclopedia of chemical technology, 4$^{th}$ ed., executive editor, J. I. Kroschwitz; editor, M. Howe-Grant, John Wiley & Sons, 1993, vol. 15, p. 518-562, incorporated herein by reference, including citations on pages 551-562. Preferred chemiluminescent dyes are acridiniumesters.

Finally, the invention also relates to the hybridoma cell lines deposited at the DSMZ under accession number DSM ACC2993, DSM ACC2996 and DSM ACC2997. These hybridoma cell lines produce the preferred antibodies of the present invention directed against the N-terminal epitopes particularly 21 to 40 and 25 to 37 of PCT and have been created as set out in Example 1.

DESCRIPTION OF DRAWINGS

FIG. 5: Amino acid sequence of Procalcitonin (PCT) (SEQ ID NO:1)

EXAMPLES

Example 1

Figure 1:
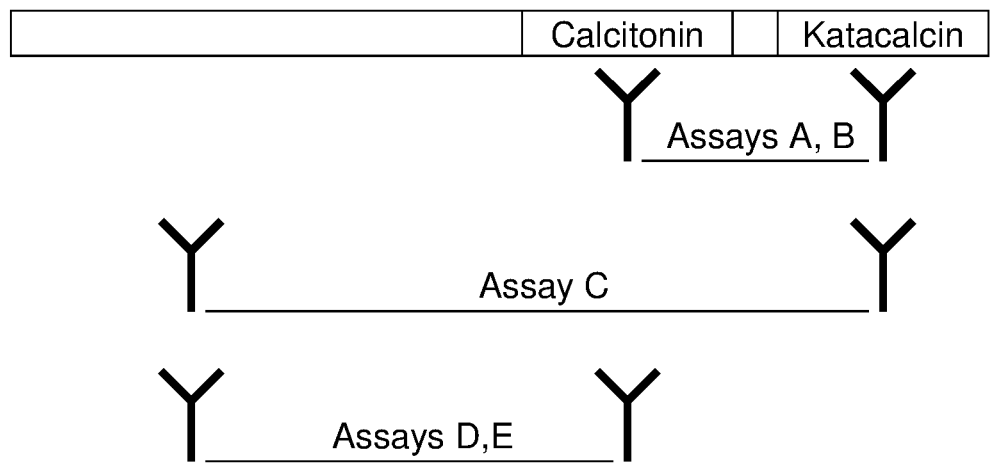
FIG. 1: Schematic representation of assays (C, D and E) used in comparison to existing assays (A and B: B•R•A•H•M•S PCT LIA and B•R•A•H•M•S PCT sensitive LIA, respectively). PCT with its calcitonin and katacalcin moieties is depicted, and antibodies with their epitopes are shown. A and B: One antibody is directed against the calcitonin moiety and the other antibody is directed against the katacalcin moiety of PCT; C: Assay, wherein one antibody is directed against an epitope in the sequence spanning amino acid residues 21-40 of PCT and the other antibody is directed against the katacalcin moiety of PCT. D, E: Assay, wherein one antibody is directed against an epitope in the sequence spanning amino acid residues 21-40 of PCT and the other antibody is directed against the calcitonin moiety of PCT.

Material and Methods
A. Development of Monoclonal Antibodies

Monoclonal antibodies against PCT were generated by genetic immunization following principally a described procedure (Costagliola et al., J Immunol 1998; 160:1458-65). In brief, the PCT coding sequence was cloned by standard procedures in vector pcDNAIII (Invitrogen, Karlsruhe, Germany). BALB/c mice were injected in the anterior tibialis muscle on day 0 with 100 mg of pcDNAIII-PCT in 25% sucrose. Injections were repeated 3 and 6 wk thereafter. Blood samples were obtained from retro-ocular capillaries 8 and 11 wk after the initial immunization and at sacrifice, which was after 18 wk, when the spleens and thyroids were also removed. Spleen cells were fused with SP2/0 myeloma cells to generate hybridoma cell lines. Cell lines were screened for their ability to secrete antibodies that would bind to immobilized recombinant human PCT (InVivo GmbH, Hennigsdorf, Germany). With this approach, cell lines secreting monoclonal antibodies FX7A7 (produced by the hybridoma cell line deposited on Jun. 4, 2009 at the DSMZ under accession number DSM ACC2997), FW5H6 (produced by the hybridoma cell line deposited on Jun. 4, 2009 at the DSMZ under accession number DSM ACC2996) and FX1G5 (produced by the hybridoma cell line deposited on Apr. 29, 2009 at the DSMZ under accession number DSM ACC2993) were generated.

B. Epitope Mapping

The mapping of epitopes within PCT of the three monoclonal antibodies FX7A7, FW5H6 and FX1G5 was done on peptide microarrays by standard procedures (JPT GmbH, Berlin, Germany). The peptide microarray was composed of 74 peptides displayed as overlapping peptide scans (format 13/11: 53 peptides; format 20/15: 21 peptides) and thus

---

Sequences

SEQ ID NO: 1 (amino acid sequence of PCT):
```
  1 APFRSALESS PADPATLSED EARLLLAALV QDYVQMKASE LEQEQEREGS

51 SLDSPRSKRC GNLSTCMLGT YTQDFNKFHT FPQTAIGVGA PGKKRDMSSD

101 LERDHRPHVS MPQNAN
``` covering the entire PCT sequence on a glass surface. The microarrays were pre-treated with blocking buffer (Pierce, Superblock; 2 h at room temperature) followed by washings with TBS buffer pH 8 and water (3 times each). Each pre-treated microarray was scanned using Axon GENEPIX 4000B Scanner for background control (no signals could be detected). Individual microarrays were incubated with antibodies in assay buffer (final concentration 60 µg/mL in Pierce Superblock buffer; total assay volume 350 µL, incubation time 3 h). Microarrays were washed with TBS buffer pH 8 followed by an incubation with fluorescence labelled secondary antibody (anti-mouse-DYLIGHT-647; Pierce 31015, 1 µg/mL, incubation time 45 min). Control incubation with fluorescence labelled secondary antibody (anti-mouse-DYLIGHT-647; Pierce 31015, 1 µg/mL, incubation time 45 min) were performed in parallel to the described experiment. Microarrays were scanned using Axon GENEPIX 4000B Scanner with appropriate wavelength settings. SPOT recognition software package ARRAYPRO was used for data analysis. Mean of signal intensities (corrected for local background) from 3 identical subarrays on each microarray image were used for data evaluation.

C. Immunoassays

Sandwich Immunoassays in the Chemiluminesce-/Coated Tube Format were Set Up as Follows:

Assay A:

A commercially available sandwich assay for PCT was used (BRAHMS PCT LIA sensitive), which uses one antibody directed against the katacalcin moiety of PCT as solid phase, and one antibody directed against the calcitonin moiety of PCT as labeled antibody (BRAHMS AG, Hennigsdorf, Germany). Recombinant PCT in various concentrations is used as standards. For the comparison with Assay E (see below), incubation conditions were adapted to those described for Assay E; i.e. 50 µl sample and 200 µl labeled antibody solution were used and incubated in a one step reaction in test tubes for 30 minutes or 2 hours.

Assay B:

A commercially available sandwich assay for PCT was used (BRAHMS PCT LIA), which uses one antibody directed against the katacalcin moiety of PCT as solid phase, and one monoclonal antibody directed against the calcitonin moiety of PCT as labeled antibody (BRAHMS AG, Hennigsdorf, Germany). Recombinant PCT in various concentrations is used as standards. For the comparison with Assay E (see below), incubation conditions were adapted to those described for Assay E; i.e. 50 µl sample and 200 µl labeled antibody solution were used and incubated in a one step reaction in test tubes for 30 minutes or 2 hours.

For the other assays, assay components were generated as follows:

Labeling of Antibodies

Labeling of antibody FX1G5 was done by standard procedures (EP 1488209, EP 1738178): The concentration of the purified antibody was adjusted to 1 g/L, and the antibody was labeled by incubation with the chemiluminescent label MACN-Acridinium-NHS-Ester (1 g/L; InVent GmbH, Hennigsdorf, Germany) in a 1:5 molar ratio for 20 min at room temperature. The reaction was stopped by addition of 1/10 volume of 50 mmol/L glycine for 10 min at room temperature. Labeled antibody was separated from free label by size-exclusion chromatography on a NAP-5 column (GE Healthcare, Freiburg, Germany) and a Bio-Sil® SEC-400-5 HPLC column (BIO-RAD).

Coating of Antibodies

Coating of a monoclonal antibody directed against the calcitonin moiety of PCT (BRAHMS AG, Hennigsdorf, Germany) was done by standard procedures (EP 1488209, EP 1738178): Polystyrene STARTUBEs (Greiner) were coated with purified antibody (per tube, 2 µg of antibody in 300 µL of 10 mmol/L Tris, 100 mmol/L NaCl, pH 7.8) overnight at 22° C. Tubes were then blocked with 10 mmol/L sodium phosphate (pH 6.5) containing 30 g/L KARION FP (Merck), 5 g/L bovine serum albumin protease free (Sigma) and lyophilized.

With these components the following assays were set up:

Assay C:

Tubes coated with an anti-katacalcin antibody and standards (recombinant PCT) were taken from the assay B.R.A.H.M.S PCT LIA sensitive (B.R.A.H.M.S AG, Hennigsdorf, Germany). MACN labeled antibody FX1G5 was used as labeled antibody. The assay buffer was 300 mmol/L potassium phosphate, pH 7.0, 100 mmol/L NaCl, 10 mmol/L EDTA, 0.9 g/L sodium azide, 5 g/L bovine serum albumin protease free (Sigma), 1 g/L nonspecific bovine IgG, 1 g/L nonspecific sheep IgG, 1 g/L nonspecific mouse IgG and contained $2 \times 10^6$ relative light units (RLU) of MACN-labeled antibody per 200 µl. 100 µl standards or samples and 200 µl assay buffer containing the MACN-labeled antibody were pipetted in the coated tubes. Tubes were incubated 2 hours at 22° C. under agitation. Then, the tubes were washed 5 times with 1 mL of B.R.A.H.M.S washing solution (B.R.A.H.M.S AG, Hennigsdorf, Germany) and bound chemiluminescence was measured for 1 s per tube with a LB952T luminometer (Berthold). Concentrations of samples were calculated using the Software MULTICALC (Spline Fit).

Assay D:

Tubes coated with an anti-calcitonin antibody were used. Standards (recombinant PCT) were taken from the assay BRAHMS PCT LIA sensitive (BRAHMS AG, Hennigsdorf, Germany). MACN labeled antibody FX1G5 was used as labeled antibody. The assay buffer was 300 mmol/L potassium phosphate, pH 7.0, 100 mmol/L NaCl, 10 mmol/L EDTA, 0.9 g/L sodium azide, 5 g/L bovine serum albumin protease free (Sigma), 1 g/L nonspecific bovine IgG, 1 g/L nonspecific sheep IgG, 1 g/L nonspecific mouse IgG and contained $2 \times 10^6$ relative light units (RLU) of MACN-labeled antibody per 200 µl. 100 µl standards or samples and 200 µl assay buffer containing the MACN-labeled antibody were pipetted in the coated tubes. Tubes were incubated 2 hours at 22° C. under agitation. Then, the tubes were washed 5 times with 1 mL of B.R.A.H.M.S washing solution (B.R.A.H.M.S AG, Hennigsdorf, Germany) and bound chemiluminescence was measured for 1 s per tube with a LB952T luminometer (Berthold). Concentrations of samples were calculated using the Software MULTICALC (Spline Fit).

Assay E:

Tubes coated with FX1G5 antibody were used. Standards (recombinant PCT) and labeled polyclonal anti-Calcitonin antibody were taken from the assay BRAHMS PCT LIA sensitive (BRAHMS AG, Hennigsdorf, Germany) 50 µl standards or samples and 200 µl assay buffer containing the MACN-labeled antibody were pipetted in the coated tubes. Tubes were incubated for either 30 minutes or 2 hours at 22° C. under agitation. Then, the tubes were washed 5 times with 1 mL of B.R.A.H.M.S washing solution (B.R.A.H.M.S AG, Hennigsdorf, Germany) and bound chemiluminescence was measured for 1 s per tube with a LB952T luminometer (Berthold).

D. Size Exclusion Chromatography

Plasma samples from nine patients with elevated PCT concentrations (including patients with sepsis) were fractionated using a Bio-Sil® SEC-125-5 HPLC column (BIO-RAD) HPLC column. The sample volume was 100 µl. The running buffer was PBS pH 7.4. The flow rate was 0.8 mL/min. 0.4 mL fractions were collected measured in assays A, C, D. The following peptides were used as calibrators: recombinant PCT (MW=ca. 13 kDa; InVivo GmbH, Hennigsdorf, Germany), preproADM 45-92 (Sequence ELRMSS SYPTGLADVK AGPAQTLIRP QDMKGASRSP EDSSPDAARI RV (SEQ ID NO: 2); MW=5.1 kDa; JPT GmbH, Berlin, Germany), Vitamin B12 (MW 1.3 kDa). Recombinant PCT and preproADM 45-92 were resolved in standard matrix obtained from the assays BRAHMS PCT LIA sensitive and BRAHMS MR-proADM LIA (BRAHMS AG, Hennigsdorf, Germany), and their elution profile of the size fractionation HPLC was determined using these assays. Vitamin B12 was diluted in running buffer and subjected to chromatography; absorption at 280 nm was recorded.

E. Measurement of Samples

Thirty serum samples of patients with local bacterial infections, sepsis, septic shock were measured in assays A, C, D.

Results

Monoclonal Antibodies

Three mouse monoclonal antibodies were generated by genetic immunization employing the entire PCT coding sequence. The epitope mapping revealed similar, albeit not identical results for all three antibodies (Table 2). Antibodies FW5H6 and FX7A7 showed maximal binding to peptide EARLLLAALVQDYVQMKASE (SEQ ID NO: a1 (pos. 21-40 within PCT), and for antibody FX1G5 maximum binding was observed on a peptide derived from the previous one, i.e. LLAALVQDYVQMK (SEQ ID NO: 4) (pos. 25-37). Outside these regions, no other significant binding sites within the PCT sequence were identified for the three antibodies. The immunization method used here is only one example. Other methods are well known, which could be applied alternatively to generate antibodies against an epitope in the described regions, and more generally upstream from position 53, for instance chemically synthesized peptides conjugated to a carrier protein could be used as antigen.

Size Exclusion Chromatography

Figure 2:
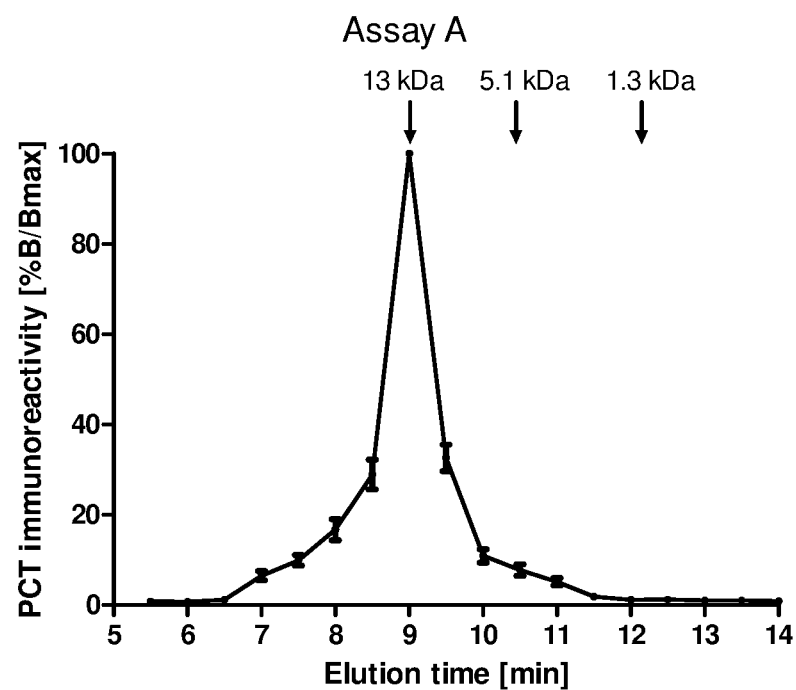
FIG. 2: PCT immunoreactivity profiles of size-fractionated PCT containing sera. Fractions were measured in Assays A (designation as in FIG. 1), and measured values were related to the maximal measured value for each assay within each fractionation run. Shown are the means+standard error (SEM).
Figure 3:
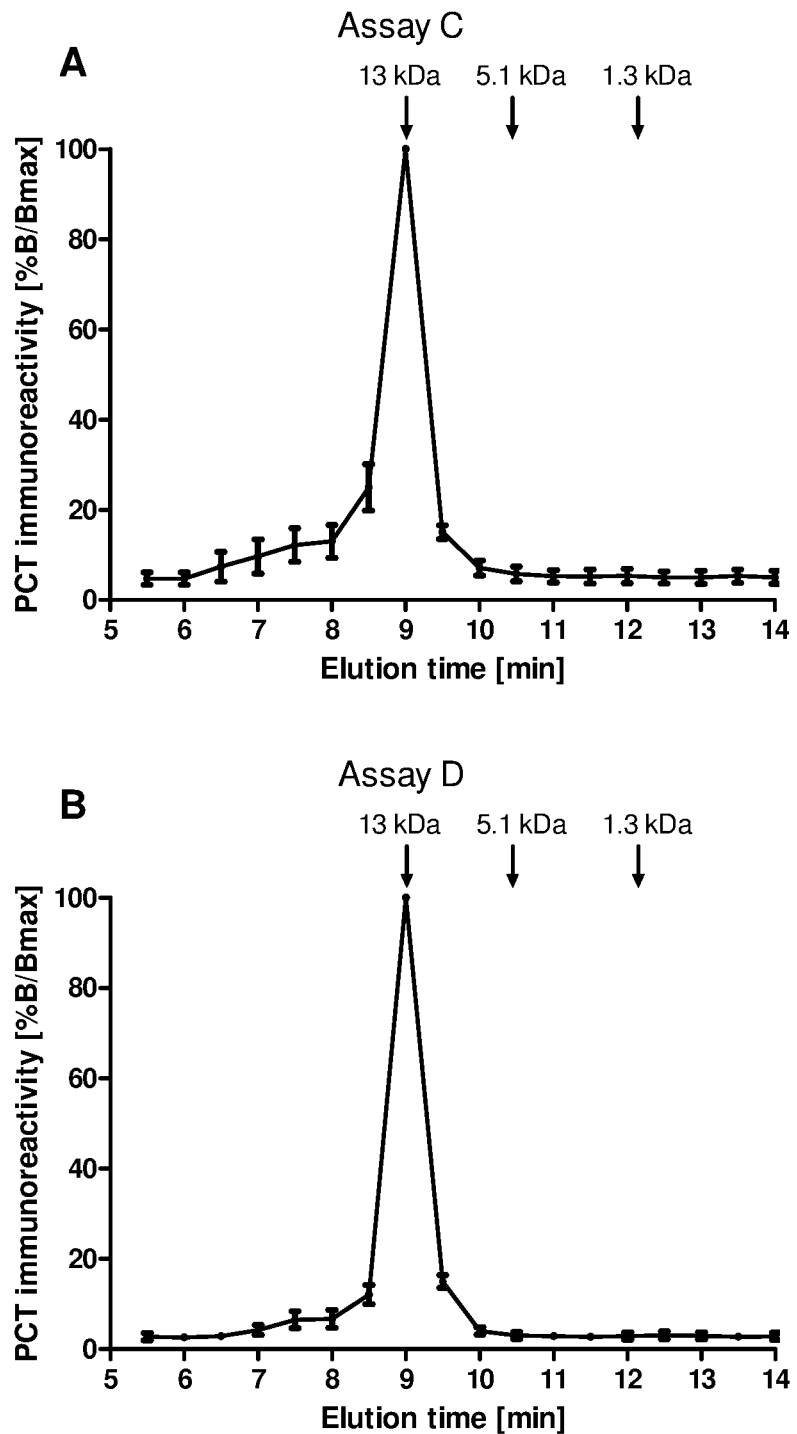
FIG. 3: PCT immunoreactivity profiles of size-fractionated PCT containing sera. Fractions were measured in Assays C and D (Panels A and B, respectively; designations as in FIG. 1), and measured values were related to the maximal measured value for each assay within each fractionation run. Shown are the means+standard error (SEM).

The apparent molecular weight of native PCT and the detectability with various sandwich immunoassays was assessed by fractionation of serum samples from patients with elevated native PCT concentrations (including sepsis patients) using size exclusion HPLC. Essentially the same immunoreactivity profile was observed, whether fractions were measured with assay A, C or D (FIG. 1): The elution time of native PCT was indistinguishable from that of recombinant PCT (13 kDa) (FIGS. 2 and 3). Virtually no PCT immunoreactivity corresponding to a molecular weight smaller than 13 kDa was detected by any of the three assays. Most notably, no PCT immunoreactivity corresponding to a molecular weight of ca. 6 kDa was detected by Assay A; this would have been expected, if the assumptions in the state of art were correct, that PCT can be split just upstream from the calcitonin moiety of PCT. These results demonstrate that, opposed to speculations in the state of the art, in patients with elevated PCT concentrations (excluding medullary thyroid carcinoma) PCT is not detectably cleaved in the middle of the molecule, and that sandwich immunoassays of the A, C or D-type detect the same antigen.

Measurement of Samples

Thirty serum samples of patients with local bacterial infections, sepsis, septic shock were measured in assays A, C, D. The Spearman correlation coefficients came out as follows: Assay A vs. C: r=0.9893; Assay A vs. D: r=0.9844. These ideal correlation coefficients derived from the measurement of a significant number of samples from patients having infections at various degrees of severity clearly confirm the results obtained by size exclusion chromatography so that one has to conclude generally that PCT, when elevated over normal (excluding medullary thyroid carcinoma), is not cleaved in the middle of the molecule.

Assay Characteristics

Figure 4:
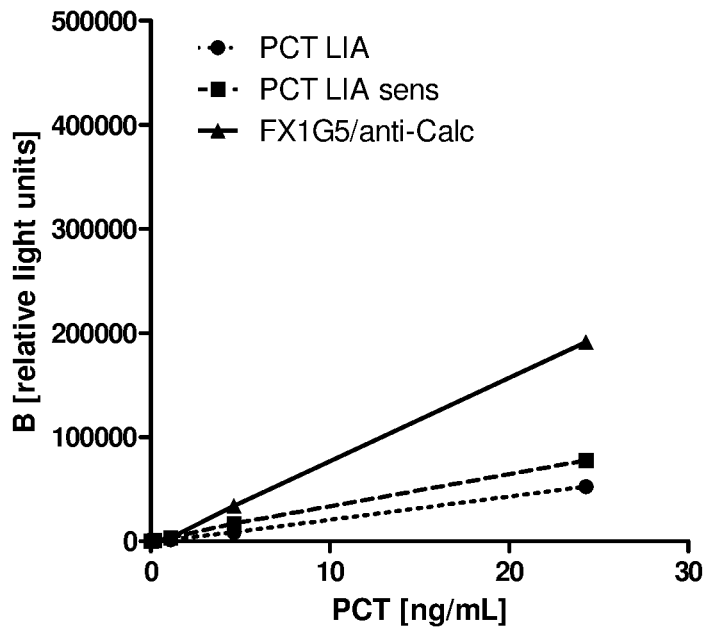
FIG. 4: Dose response curves for three PCT sandwich immunoassays. The assays were incubated for 30 minutes (panel A) or 2 hours (panel B). PCT LIA and PCT LIA sens. correspond to B•R•A•H•M•S PCT LIA and B•R•A•H•M•S PCT sensitive LIA, respectively (designated A and B in FIG. 1). FX1G5/anti-Calc. represents assay Assay E.
Figure 4:
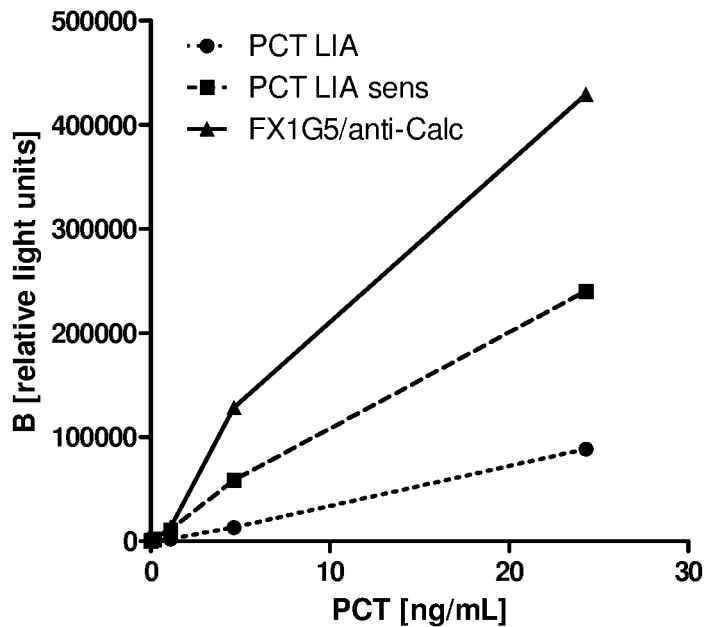

The use of one of the antibodies described in the present invention, FX1G5 having an epitope corresponding to positions 25-37 of PCT, in a sandwich assay employing an anti-Calcitonin antibody as second antibody (Assay E), was analyzed in comparison to state-of-art PCT assays, which utilize the same detection technology (coated tube/chemiluminescence label); i.e. BRAHMS PCT LIA sensitive (Assay A) and BRAHMS PCT LIA (Assay B). Surprisingly, Assay E exhibited considerably more dynamic dose-response-curves than both established assays, independent from the incubation time (FIG. 4).

TABLE 1

Described anti-PCT antibodies and their use in immunoassays

| Name | Source | Immunogen (numbers refer to amino acid positions in PCT 1-116) | Epitope (numbers refer to amino acid positions in PCT 1-116) | tested in sandwich immuno-assay | tested with native PCT | Reference |
|---|---|---|---|---|---|---|
| anti-Calcitonin | Sheep | Calcitonin | GTYTQDFNKFH; 69-79 (SEQ ID NO: 5) | yes | yes | (Morgenthaler, et al. Clin Chem 2002; 48: 788-90) |
| anti-katacalcin (QN05) | mouse | Katacalcin | ERDHRPHVSM; 102-111 (SEQ ID NO: 6) | yes | yes | (Morgenthaler, et al. Clin Chem 2002; 48: 788-90) |
| PROC1 3G3 | rat | FRSALESSPADPATLSEDE; 3-20 (SEQ ID NO: 7) | n.d. | yes | no | (Kramer, et al. Anal Bioanal Chem 2008; 392: 727-36) |
| PROC4 6C6 etc | rat | SDLERDHRPHV; 99-109 (SEQ ID NO: 8) | n.d. | yes | no | (Kramer, et al. Anal Bioanal Chem 2008; 392: 727-36) |

TABLE 1-continued

Described anti-PCT antibodies and their use in immunoassays

| Name | Source | Immunogen (numbers refer to amino acid positions in PCT 1-116) | Epitope (numbers refer to amino acid positions in PCT 1-116) | tested in sandwich immuno-assay | tested with native PCT | Reference |
|---|---|---|---|---|---|---|
| R2B7 antiserum | rabbit | Amino-ProCT; 1-57 | n.d. | no | yes | (Whang, et al. J Clin Endocrinol Metab 1998; 83: 3296-301) |
| 295/3H12 etc. | mouse | APFRLSALESC; 1-9 (SEQ ID NO: 9) | n.d. other than N-terminal Alanin being required | yes | yes | DE 10 2007 009 751 |
| 98-47/44 | mouse | DSPRSKRCGNLS; 53-64 (SEQ ID NO: 10) | n.d. | yes | yes | U.S. Pat. No. 6,451,311 |
| 98-31/04 | mouse | VGAPGKKRDMSS; 88-99 (SEQ ID NO: 11) | n.d. | yes | yes | U.S. Pat. No. 6,451,311 |
| CT08 | mouse | Calcitonin | TYTQDFN; 70-76 (SEQ ID NO: 12) | yes | yes | (Assicot, et al. Lancet 1993; 341: 515-8; Ghillani et al, Cancer Res 1989; 49: 6845-51) |
| KC01 | mouse | Katacalcin | DMSSDLERDHR; 96-106 (SEQ ID NO: 13) | yes | yes | (Assicot, et al. Lancet 1993; 341: 515-8; Ghillani, et al. Cancer Res 1989; 49: 6845-51) |

TABLE 2

Epitope mapping results: Observed binding signals for the three antibodies to the shown peptides representing subsequences of the entire PCT sequence were related to the maximum binding obtained per antibody (B/Bmax).

| peptide # | sequence | SEQ ID NO: | FX1G5 | FW5H6 | FX7A7 |
|---|---|---|---|---|---|
| 1 | APFRSALESSPAD | 14 | 0.0% | 0.0% | 0.0% |
| 2 | FRSALESSPADPA | 15 | 0.0% | 0.0% | 0.0% |
| 3 | SALESSPADPATL | 16 | 0.0% | 0.0% | 0.0% |
| 4 | LESSPADPATLSE | 17 | 0.0% | 0.0% | 0.0% |
| 5 | SSPADPATLSEDE | 18 | 0.0% | 0.0% | 0.0% |
| 6 | PADPATLSEDEAR | 19 | 0.0% | 0.0% | 0.0% |
| 7 | DPATLSEDEARLL | 20 | 0.0% | 0.0% | 0.0% |
| 8 | ATLSEDEARLLLA | 21 | 0.0% | 0.1% | 0.0% |
| 9 | LSEDEARLLLAAL | 22 | 3.0% | 0.0% | 0.0% |
| 10 | EDEARLLLAALVQ | 23 | 0.3% | 0.0% | 0.0% |
| 11 | EARLLLAALVQDY | 24 | 1.7% | 0.0% | 0.0% |
| 12 | RLLLAALVQDYVQ | 25 | 25.0% | 57.3% | 0.2% |
| 13 | LLAALVQDYVQMK | 26 | 100.0% | 59.5% | 62.7% |
| 14 | AALVQDYVQMKAS | 27 | 11.9% | 14.7% | 0.0% |
| 15 | LVQDYVQMKASEL | 28 | 0.0% | 0.0% | 0.0% |
| 16 | QDYVQMKASELEQ | 29 | 0.0% | 0.0% | 0.0% |

TABLE 2-continued

Epitope mapping results: Observed binding signals for the three antibodies to the shown peptides representing subsequences of the entire PCT sequence were related to the maximum binding obtained per antibody (B/Bmax).

| peptide # | sequence | SEQ ID NO: | FX1G5 | FW5H6 | FX7A7 |
|---|---|---|---|---|---|
| 17 | YVQMKASELEQEQ | 30 | 0.0% | 0.0% | 0.0% |
| 18 | QMKASELEQEQER | 31 | 0.0% | 0.0% | 0.0% |
| 19 | KASELEQEQEREG | 32 | 0.0% | 0.0% | 0.0% |
| 20 | SELEQEQEREGSS | 33 | 0.0% | 0.0% | 0.0% |
| 21 | LEQEQEREGSSLD | 34 | 0.0% | 0.1% | 0.0% |
| 22 | QEQEREGSSLDSP | 35 | 0.0% | 0.0% | 0.0% |
| 23 | QEREGSSLDSPRS | 36 | 0.0% | 0.0% | 0.0% |
| 24 | REGSSLDSPRSKR | 37 | 0.0% | 0.1% | 0.0% |
| 25 | GSSLDSPRSKRCG | 38 | 0.0% | 0.3% | 0.1% |
| 26 | SLDSPRSKRCGNL | 39 | 0.0% | 0.2% | 0.3% |
| 27 | DSPRSKRCGNLST | 40 | 0.0% | 0.0% | 0.2% |
| 28 | PRSKRCGNLSTCM | 41 | 0.0% | 0.0% | 0.2% |
| 29 | SKRCGNLSTCMLG | 42 | 0.0% | 0.0% | 0.0% |
| 30 | RCGNLSTCMLGTY | 43 | 0.0% | 0.0% | 0.2% |
| 31 | GNLSTCMLGTYTQ | 44 | 0.1% | 0.0% | 0.0% |
| 32 | LSTCMLGTYTQDF | 45 | 0.0% | 0.0% | 0.0% |
| 33 | TCMLGTYTQDFNK | 46 | 0.0% | 0.0% | 0.0% |
| 34 | MLGTYTQDFNKFH | 47 | 0.0% | 3.4% | 0.0% |
| 35 | GTYTQDFNKFHTF | 48 | 0.0% | 1.9% | 0.0% |
| 36 | YTQDFNKFHTFPQ | 49 | 0.0% | 0.1% | 0.0% |
| 37 | QDFNKFHTFPQTA | 50 | 0.4% | 0.0% | 0.0% |
| 38 | FNKFHTFPQTAIG | 51 | 0.0% | 0.1% | 0.0% |
| 39 | KFHTFPQTAIGVG | 52 | 0.2% | 0.0% | 0.0% |
| 40 | HTFPQTAIGVGAP | 53 | 0.0% | 0.0% | 0.0% |
| 41 | FPQTAIGVGAPGK | 54 | 0.1% | 0.0% | 0.0% |
| 42 | QTAIGVGAPGKKR | 55 | 1.0% | 0.1% | 0.1% |
| 43 | AIGVGAPGKKRDM | 56 | 0.0% | 0.0% | 0.0% |
| 44 | GVGAPGKKRDMSS | 57 | 0.0% | 0.0% | 0.0% |
| 45 | GAPGKKRDMSSDL | 58 | 0.0% | 0.6% | 0.0% |
| 46 | PGKKRDMSSDLER | 59 | 0.0% | 0.3% | 0.1% |
| 47 | KKRDMSSDLERDH | 60 | 0.0% | 0.0% | 0.0% |
| 48 | RDMSSDLERDHRP | 61 | 0.0% | 1.5% | 0.0% |
| 49 | MSSDLERDHRPHV | 62 | 1.8% | 1.5% | 1.9% |
| 50 | SDLERDHRPHVSM | 63 | 0.4% | 1.5% | 0.9% |
| 51 | LERDHRPHVSMPQ | 64 | 1.3% | 1.5% | 2.8% |
| 52 | RDHRPHVSMPQNA | 65 | 0.0% | 0.1% | 0.2% |

TABLE 2 -continued

Epitope mapping results: Observed binding signals for the three antibodies to the shown peptides representing subsequences of the entire PCT sequence were related to the maximum binding obtained per antibody (B/Bmax).

| peptide # | sequence | SEQ ID NO: | FX1G5 | FW5H6 | FX7A7 |
|---|---|---|---|---|---|
| 53 | DHRPHVSMPQNAN | 66 | 0.0% | 0.0% | 0.0% |
| 54 | APFRSALESSPADPATLSED | 67 | 0.2% | 0.0% | 0.0% |
| 55 | ALESSPADPATLSEDEARLL | 68 | 0.3% | 0.1% | 0.0% |
| 56 | PADPATLSEDEARLLLAALV | 69 | 0.0% | 0.0% | 0.0% |
| 57 | TLSEDEARLLLAALVQDYVQ | 70 | 64.4% | 64.7% | 49.9% |
| 58 | EARLLLAALVQDYVQMKASE | 71 | 74.6% | 100.0% | 100.0% |
| 59 | LAALVQDYVQMKASELEQEQ | 72 | 2.8% | 2.7% | 0.1% |
| 60 | QDYVQMKASELEQEQEREGS | 73 | 0.7% | 0.0% | 0.1% |
| 61 | MKASELEQEQEREGSSLDSP | 74 | 0.6% | 0.0% | 0.1% |
| 62 | LEQEQEREGSSLDSPRSKRC | 75 | 0.0% | 0.4% | 0.1% |
| 63 | EREGSSLDSPRSKRCGNLST | 76 | 0.0% | 0.2% | 0.0% |
| 64 | SLDSPRSKRCGNLSTCMLGT | 77 | 0.5% | 0.0% | 0.0% |
| 65 | RSKRCGNLSTCMLGTYTQDF | 78 | 0.9% | 0.2% | 0.0% |
| 66 | GNLSTCMLGTYTQDFNKFHT | 79 | 0.0% | 0.5% | 0.0% |
| 67 | CMLGTYTQDFNKFHTFPQTA | 80 | 0.0% | 0.1% | 0.0% |
| 68 | YTQDFNKFHTFPQTAIGVGA | 81 | 0.0% | 0.0% | 0.0% |
| 69 | NKFHTFPQTAIGVGAPGKKR | 82 | 4.8% | 0.3% | 0.9% |
| 70 | FPQTAIGVGAPGKKRDMSSD | 83 | 0.0% | 0.0% | 0.0% |
| 71 | IGVGAPGKKRDMSSDLERDH | 84 | 0.0% | 0.1% | 0.0% |
| 72 | PGKKRDMSSDLERDHRPHVS | 85 | 0.7% | 0.1% | 2.3% |
| 73 | DMSSDLERDHRPHVSMPQNA | 86 | 0.2% | 0.1% | 0.3% |
| 74 | MSSDLERDHRPHVSMPQNAN | 87 | 0.3% | 0.4% | 0.2% |

The invention claimed is:

1. An in vitro method for the detection of SEQ ID NO:1 (Procalcitonin), or a fragment of SEQ ID NO:1 having a length of at least 20 amino acid residues, in a biological sample derived from a bodily fluid obtained from a subject, said fragment of SEQ ID NO:1 containing an epitope in the sequence spanning amino acid residues 25 to 37 of SEQ ID NO:1 and: an epitope in the sequence spanning amino acid residues 96 to 116 of SEQ ID NO:1, and/or an epitope in the sequence spanning amino acid residues 60 to 91 of SEQ ID NO:1; said method comprising:
  a. contacting said sample with at least two antibodies or antigen binding fragments thereof directed against different epitopes within SEQ ID NO:1 (Procalcitonin), and
  b. qualitatively or quantitatively detecting binding of said at least two antibodies to SEQ ID NO:1 (Procalcitonin), or said fragment thereof, wherein binding indicates the presence or concentration of Procalcitonin or said fragment in said sample,
  wherein one of said at least two antibodies or antigen binding fragment thereof is directed against an epitope in the sequence spanning amino acid residues 25 to 37 of SEQ ID NO:1, wherein said one antibody is produced by a hybridoma cell line that is deposited at the DSMZ under accession number DSM ACC2993, and
  wherein another of said at least two antibodies or antigen binding fragment thereof is directed against an epitope in the sequence spanning amino acid residues 96 to 116 of SEQ ID NO:1, or is directed against an epitope in the sequence spanning amino acid residues 60 to 91 of SEQ ID NO:1, and wherein said another of said at least two antibodies is a monoclonal antibody.

2. The method of claim 1, wherein said another of said at least two antibodies or antigen binding fragment thereof is directed against an epitope in the sequence spanning amino acid residues 96 to 116 of SEQ ID NO:1.

3. The method according to claim 1, wherein said another of said at least two antibodies or antigen binding fragment thereof is directed against an epitope in the sequence spanning amino acid residues 60 to 91 of SEQ ID NO:1.

4. An antibody or an antigen binding fragment thereof directed against an epitope in the sequence spanning amino acid residues 25 to 37 of SEQ ID NO:1 (Procalcitonin), wherein the antibody is produced by a hybridoma cell line that is deposited at the DSMZ under accession number DSM ACC2993.

5. A kit comprising:
  a first antibody or an antigen binding fragment thereof directed against an epitope in the sequence spanning amino acid residues 25 to 37 of SEQ ID NO:1, wherein said first antibody is produced by a hybridoma cell line that is deposited at the DSMZ under accession number DSM ACC2993, and
  a second antibody or an antigen binding fragment thereof directed against an epitope in the sequence spanning amino acid residues 96 to 116 of SEQ ID NO:1 or 60 to 91 of SEQ ID NO:1, and wherein said second antibody is a monoclonal antibody.

6. The kit of claim 5, wherein the second antibody is directed against an epitope in the sequence spanning amino acid residues 60 to 91 of SEQ ID NO:1.

7. A method of performing a sandwich immunoassay for the detection and/or quantification of Procalcitonin in a biological sample from a bodily fluid, said method comprising detecting or determining the amount of Procalcitonin in said biological sample using the kit of claim 5.

8. The hybridoma cell line deposited at the DSMZ under accession number DSM ACC2993.

9. The kit of claim 5, wherein the second antibody is directed against an epitope in the sequence spanning amino acid residues 96 to 116 of SEQ ID NO:1.

* * * * *

SEQUENCE LISTING

<160> NUMBER OF SEQ ID NOS: 87

<210> SEQ ID NO 1
<211> LENGTH: 116
<212> TYPE: PRT
<213> ORGANISM: Homo sapiens

<400> SEQUENCE: 1

```
Ala Pro Phe Arg Ser Ala Leu Glu Ser Ser Pro Ala Asp Pro Ala Thr
1               5                   10                  15

Leu Ser Glu Asp Glu Ala Arg Leu Leu Leu Ala Ala Leu Val Gln Asp
            20                  25                  30

Tyr Val Gln Met Lys Ala Ser Glu Leu Glu Gln Glu Gln Glu Arg Glu
        35                  40                  45

Gly Ser Ser Leu Asp Ser Pro Arg Ser Lys Arg Cys Gly Asn Leu Ser
    50                  55                  60
```

```
Thr Cys Met Leu Gly Thr Tyr Thr Gln Asp Phe Asn Lys Phe His Thr
 65                  70                  75                  80

Phe Pro Gln Thr Ala Ile Gly Val Gly Ala Pro Gly Lys Lys Arg Asp
                 85                  90                  95

Met Ser Ser Asp Leu Glu Arg Asp His Arg Pro His Val Ser Met Pro
            100                 105                 110

Gln Asn Ala Asn
        115

<210> SEQ ID NO 2
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Leu Arg Met Ser Ser Ser Tyr Pro Thr Gly Leu Ala Asp Val Lys
 1               5                  10                  15

Ala Gly Pro Ala Gln Thr Leu Ile Arg Pro Gln Asp Met Lys Gly Ala
                20                  25                  30

Ser Arg Ser Pro Glu Asp Ser Ser Pro Asp Ala Ala Arg Ile Arg Val
            35                  40                  45

<210> SEQ ID NO 3
<211> LENGTH: 20
<212> TYPE: PRT
<213> ORGANISM: Homo sapiens

<400> SEQUENCE: 3

Glu Ala Arg Leu Leu Leu Ala Ala Leu Val Gln Asp Tyr Val Gln Met
 1               5                  10                  15

Lys Ala Ser Glu
            20

<210> SEQ ID NO 4
<211> LENGTH: 13
<212> TYPE: PRT
<213> ORGANISM: Homo sapiens

<400> SEQUENCE: 4

Leu Leu Ala Ala Leu Val Gln Asp Tyr Val Gln Met Lys
 1               5                  10

<210> SEQ ID NO 5
<211> LENGTH: 11
<212> TYPE: PRT
<213> ORGANISM: Homo sapiens

<400> SEQUENCE: 5

Gly Thr Tyr Thr Gln Asp Phe Asn Lys Phe His
 1               5                  10

<210> SEQ ID NO 6
<211> LENGTH: 10
<212> TYPE: PRT
<213> ORGANISM: Homo sapiens

<400> SEQUENCE: 6

Glu Arg Asp His Arg Pro His Val Ser Met
 1               5                  10
```

```
<210> SEQ ID NO 7
<211> LENGTH: 19
<212> TYPE: PRT
<213> ORGANISM: Homo sapiens

<400> SEQUENCE: 7

Phe Arg Ser Ala Leu Glu Ser Ser Pro Ala Asp Pro Ala Thr Leu Ser
1               5                   10                  15
Glu Asp Glu

<210> SEQ ID NO 8
<211> LENGTH: 11
<212> TYPE: PRT
<213> ORGANISM: Homo sapiens

<400> SEQUENCE: 8

Ser Asp Leu Glu Arg Asp His Arg Pro His Val
1               5                   10

<210> SEQ ID NO 9
<211> LENGTH: 11
<212> TYPE: PRT
<213> ORGANISM: Homo sapiens

<400> SEQUENCE: 9

Ala Pro Phe Arg Leu Ser Ala Leu Glu Ser Cys
1               5                   10

<210> SEQ ID NO 10
<211> LENGTH: 12
<212> TYPE: PRT
<213> ORGANISM: Homo sapiens

<400> SEQUENCE: 10

Asp Ser Pro Arg Ser Lys Arg Cys Gly Asn Leu Ser
1               5                   10

<210> SEQ ID NO 11
<211> LENGTH: 12
<212> TYPE: PRT
<213> ORGANISM: Homo sapiens

<400> SEQUENCE: 11

Val Gly Ala Pro Gly Lys Lys Arg Asp Met Ser Ser
1               5                   10

<210> SEQ ID NO 12
<211> LENGTH: 7
<212> TYPE: PRT
<213> ORGANISM: Homo sapiens

<400> SEQUENCE: 12

Thr Tyr Thr Gln Asp Phe Asn
1               5

<210> SEQ ID NO 13
<211> LENGTH: 11
<212> TYPE: PRT
<213> ORGANISM: Homo sapiens

<400> SEQUENCE: 13

Asp Met Ser Ser Asp Leu Glu Arg Asp His Arg
1               5                   10
```

<210> SEQ ID NO 14
<211> LENGTH: 13
<212> TYPE: PRT
<213> ORGANISM: Homo sapiens

<400> SEQUENCE: 14

Ala Pro Phe Arg Ser Ala Leu Glu Ser Ser Pro Ala Asp
1               5                   10

<210> SEQ ID NO 15
<211> LENGTH: 13
<212> TYPE: PRT
<213> ORGANISM: Homo sapiens

<400> SEQUENCE: 15

Phe Arg Ser Ala Leu Glu Ser Ser Pro Ala Asp Pro Ala
1               5                   10

<210> SEQ ID NO 16
<211> LENGTH: 13
<212> TYPE: PRT
<213> ORGANISM: Homo sapiens

<400> SEQUENCE: 16

Ser Ala Leu Glu Ser Ser Pro Ala Asp Pro Ala Thr Leu
1               5                   10

<210> SEQ ID NO 17
<211> LENGTH: 13
<212> TYPE: PRT
<213> ORGANISM: Homo sapiens

<400> SEQUENCE: 17

Leu Glu Ser Ser Pro Ala Asp Pro Ala Thr Leu Ser Glu
1               5                   10

<210> SEQ ID NO 18
<211> LENGTH: 13
<212> TYPE: PRT
<213> ORGANISM: Homo sapiens

<400> SEQUENCE: 18

Ser Ser Pro Ala Asp Pro Ala Thr Leu Ser Glu Asp Glu
1               5                   10

<210> SEQ ID NO 19
<211> LENGTH: 13
<212> TYPE: PRT
<213> ORGANISM: Homo sapiens

<400> SEQUENCE: 19

Pro Ala Asp Pro Ala Thr Leu Ser Glu Asp Glu Ala Arg
1               5                   10

<210> SEQ ID NO 20
<211> LENGTH: 13
<212> TYPE: PRT
<213> ORGANISM: Homo sapiens

<400> SEQUENCE: 20

Asp Pro Ala Thr Leu Ser Glu Asp Glu Ala Arg Leu Leu
1               5                   10

<210> SEQ ID NO 21

```
<211> LENGTH: 13
<212> TYPE: PRT
<213> ORGANISM: Homo sapiens

<400> SEQUENCE: 21

Ala Thr Leu Ser Glu Asp Glu Ala Arg Leu Leu Leu Ala
1               5                   10

<210> SEQ ID NO 22
<211> LENGTH: 13
<212> TYPE: PRT
<213> ORGANISM: Homo sapiens

<400> SEQUENCE: 22

Leu Ser Glu Asp Glu Ala Arg Leu Leu Leu Ala Ala Leu
1               5                   10

<210> SEQ ID NO 23
<211> LENGTH: 13
<212> TYPE: PRT
<213> ORGANISM: Homo sapiens

<400> SEQUENCE: 23

Glu Asp Glu Ala Arg Leu Leu Leu Ala Ala Leu Val Gln
1               5                   10

<210> SEQ ID NO 24
<211> LENGTH: 13
<212> TYPE: PRT
<213> ORGANISM: Homo sapiens

<400> SEQUENCE: 24

Glu Ala Arg Leu Leu Leu Ala Ala Leu Val Gln Asp Tyr
1               5                   10

<210> SEQ ID NO 25
<211> LENGTH: 13
<212> TYPE: PRT
<213> ORGANISM: Homo sapiens

<400> SEQUENCE: 25

Arg Leu Leu Leu Ala Ala Leu Val Gln Asp Tyr Val Gln
1               5                   10

<210> SEQ ID NO 26
<211> LENGTH: 13
<212> TYPE: PRT
<213> ORGANISM: Homo sapiens

<400> SEQUENCE: 26

Leu Leu Ala Ala Leu Val Gln Asp Tyr Val Gln Met Lys
1               5                   10

<210> SEQ ID NO 27
<211> LENGTH: 13
<212> TYPE: PRT
<213> ORGANISM: Homo sapiens

<400> SEQUENCE: 27

Ala Ala Leu Val Gln Asp Tyr Val Gln Met Lys Ala Ser
1               5                   10

<210> SEQ ID NO 28
<211> LENGTH: 13
<212> TYPE: PRT
```

<213> ORGANISM: Homo sapiens

<400> SEQUENCE: 28

Leu Val Gln Asp Tyr Val Gln Met Lys Ala Ser Glu Leu
1               5                   10

<210> SEQ ID NO 29
<211> LENGTH: 13
<212> TYPE: PRT
<213> ORGANISM: Homo sapiens

<400> SEQUENCE: 29

Gln Asp Tyr Val Gln Met Lys Ala Ser Glu Leu Glu Gln
1               5                   10

<210> SEQ ID NO 30
<211> LENGTH: 13
<212> TYPE: PRT
<213> ORGANISM: Homo sapiens

<400> SEQUENCE: 30

Tyr Val Gln Met Lys Ala Ser Glu Leu Glu Gln Glu Gln
1               5                   10

<210> SEQ ID NO 31
<211> LENGTH: 13
<212> TYPE: PRT
<213> ORGANISM: Homo sapiens

<400> SEQUENCE: 31

Gln Met Lys Ala Ser Glu Leu Glu Gln Glu Gln Glu Arg
1               5                   10

<210> SEQ ID NO 32
<211> LENGTH: 13
<212> TYPE: PRT
<213> ORGANISM: Homo sapiens

<400> SEQUENCE: 32

Lys Ala Ser Glu Leu Glu Gln Glu Gln Glu Arg Glu Gly
1               5                   10

<210> SEQ ID NO 33
<211> LENGTH: 13
<212> TYPE: PRT
<213> ORGANISM: Homo sapiens

<400> SEQUENCE: 33

Ser Glu Leu Glu Gln Glu Gln Glu Arg Glu Gly Ser Ser
1               5                   10

<210> SEQ ID NO 34
<211> LENGTH: 13
<212> TYPE: PRT
<213> ORGANISM: Homo sapiens

<400> SEQUENCE: 34

Leu Glu Gln Glu Gln Glu Arg Glu Gly Ser Ser Leu Asp
1               5                   10

<210> SEQ ID NO 35
<211> LENGTH: 13
<212> TYPE: PRT
<213> ORGANISM: Homo sapiens

<400> SEQUENCE: 35

Gln Glu Gln Glu Arg Glu Gly Ser Ser Leu Asp Ser Pro
1               5                   10

<210> SEQ ID NO 36
<211> LENGTH: 13
<212> TYPE: PRT
<213> ORGANISM: Homo sapiens

<400> SEQUENCE: 36

Gln Glu Arg Glu Gly Ser Ser Leu Asp Ser Pro Arg Ser
1               5                   10

<210> SEQ ID NO 37
<211> LENGTH: 13
<212> TYPE: PRT
<213> ORGANISM: Homo sapiens

<400> SEQUENCE: 37

Arg Glu Gly Ser Ser Leu Asp Ser Pro Arg Ser Lys Arg
1               5                   10

<210> SEQ ID NO 38
<211> LENGTH: 13
<212> TYPE: PRT
<213> ORGANISM: Homo sapiens

<400> SEQUENCE: 38

Gly Ser Ser Leu Asp Ser Pro Arg Ser Lys Arg Cys Gly
1               5                   10

<210> SEQ ID NO 39
<211> LENGTH: 13
<212> TYPE: PRT
<213> ORGANISM: Homo sapiens

<400> SEQUENCE: 39

Ser Leu Asp Ser Pro Arg Ser Lys Arg Cys Gly Asn Leu
1               5                   10

<210> SEQ ID NO 40
<211> LENGTH: 13
<212> TYPE: PRT
<213> ORGANISM: Homo sapiens

<400> SEQUENCE: 40

Asp Ser Pro Arg Ser Lys Arg Cys Gly Asn Leu Ser Thr
1               5                   10

<210> SEQ ID NO 41
<211> LENGTH: 13
<212> TYPE: PRT
<213> ORGANISM: Homo sapiens

<400> SEQUENCE: 41

Pro Arg Ser Lys Arg Cys Gly Asn Leu Ser Thr Cys Met
1               5                   10

<210> SEQ ID NO 42
<211> LENGTH: 13
<212> TYPE: PRT
<213> ORGANISM: Homo sapiens

<400> SEQUENCE: 42

Ser Lys Arg Cys Gly Asn Leu Ser Thr Cys Met Leu Gly
1               5                   10

<210> SEQ ID NO 43
<211> LENGTH: 13
<212> TYPE: PRT
<213> ORGANISM: Homo sapiens

<400> SEQUENCE: 43

Arg Cys Gly Asn Leu Ser Thr Cys Met Leu Gly Thr Tyr
1               5                   10

<210> SEQ ID NO 44
<211> LENGTH: 13
<212> TYPE: PRT
<213> ORGANISM: Homo sapiens

<400> SEQUENCE: 44

Gly Asn Leu Ser Thr Cys Met Leu Gly Thr Tyr Thr Gln
1               5                   10

<210> SEQ ID NO 45
<211> LENGTH: 13
<212> TYPE: PRT
<213> ORGANISM: Homo sapiens

<400> SEQUENCE: 45

Leu Ser Thr Cys Met Leu Gly Thr Tyr Thr Gln Asp Phe
1               5                   10

<210> SEQ ID NO 46
<211> LENGTH: 13
<212> TYPE: PRT
<213> ORGANISM: Homo sapiens

<400> SEQUENCE: 46

Thr Cys Met Leu Gly Thr Tyr Thr Gln Asp Phe Asn Lys
1               5                   10

<210> SEQ ID NO 47
<211> LENGTH: 13
<212> TYPE: PRT
<213> ORGANISM: Homo sapiens

<400> SEQUENCE: 47

Met Leu Gly Thr Tyr Thr Gln Asp Phe Asn Lys Phe His
1               5                   10

<210> SEQ ID NO 48
<211> LENGTH: 13
<212> TYPE: PRT
<213> ORGANISM: Homo sapiens

<400> SEQUENCE: 48

Gly Thr Tyr Thr Gln Asp Phe Asn Lys Phe His Thr Phe
1               5                   10

<210> SEQ ID NO 49
<211> LENGTH: 13
<212> TYPE: PRT
<213> ORGANISM: Homo sapiens

<400> SEQUENCE: 49

Tyr Thr Gln Asp Phe Asn Lys Phe His Thr Phe Pro Gln
1               5                   10

<210> SEQ ID NO 50
<211> LENGTH: 13
<212> TYPE: PRT
<213> ORGANISM: Homo sapiens

<400> SEQUENCE: 50

Gln Asp Phe Asn Lys Phe His Thr Phe Pro Gln Thr Ala
1               5                   10

<210> SEQ ID NO 51
<211> LENGTH: 13
<212> TYPE: PRT
<213> ORGANISM: Homo sapiens

<400> SEQUENCE: 51

Phe Asn Lys Phe His Thr Phe Pro Gln Thr Ala Ile Gly
1               5                   10

<210> SEQ ID NO 52
<211> LENGTH: 13
<212> TYPE: PRT
<213> ORGANISM: Homo sapiens

<400> SEQUENCE: 52

Lys Phe His Thr Phe Pro Gln Thr Ala Ile Gly Val Gly
1               5                   10

<210> SEQ ID NO 53
<211> LENGTH: 13
<212> TYPE: PRT
<213> ORGANISM: Homo sapiens

<400> SEQUENCE: 53

His Thr Phe Pro Gln Thr Ala Ile Gly Val Gly Ala Pro
1               5                   10

<210> SEQ ID NO 54
<211> LENGTH: 13
<212> TYPE: PRT
<213> ORGANISM: Homo sapiens

<400> SEQUENCE: 54

Phe Pro Gln Thr Ala Ile Gly Val Gly Ala Pro Gly Lys
1               5                   10

<210> SEQ ID NO 55
<211> LENGTH: 13
<212> TYPE: PRT
<213> ORGANISM: Homo sapiens

<400> SEQUENCE: 55

Gln Thr Ala Ile Gly Val Gly Ala Pro Gly Lys Lys Arg
1               5                   10

<210> SEQ ID NO 56
<211> LENGTH: 13
<212> TYPE: PRT
<213> ORGANISM: Homo sapiens

<400> SEQUENCE: 56

Ala Ile Gly Val Gly Ala Pro Gly Lys Lys Arg Asp Met
1               5                   10

<210> SEQ ID NO 57
<211> LENGTH: 13
<212> TYPE: PRT
<213> ORGANISM: Homo sapiens

<400> SEQUENCE: 57

Gly Val Gly Ala Pro Gly Lys Lys Arg Asp Met Ser Ser
1               5                   10

<210> SEQ ID NO 58
<211> LENGTH: 13
<212> TYPE: PRT
<213> ORGANISM: Homo sapiens

<400> SEQUENCE: 58

Gly Ala Pro Gly Lys Lys Arg Asp Met Ser Ser Asp Leu
1               5                   10

<210> SEQ ID NO 59
<211> LENGTH: 13
<212> TYPE: PRT
<213> ORGANISM: Homo sapiens

<400> SEQUENCE: 59

Pro Gly Lys Lys Arg Asp Met Ser Ser Asp Leu Glu Arg
1               5                   10

<210> SEQ ID NO 60
<211> LENGTH: 13
<212> TYPE: PRT
<213> ORGANISM: Homo sapiens

<400> SEQUENCE: 60

Lys Lys Arg Asp Met Ser Ser Asp Leu Glu Arg Asp His
1               5                   10

<210> SEQ ID NO 61
<211> LENGTH: 13
<212> TYPE: PRT
<213> ORGANISM: Homo sapiens

<400> SEQUENCE: 61

Arg Asp Met Ser Ser Asp Leu Glu Arg Asp His Arg Pro
1               5                   10

<210> SEQ ID NO 62
<211> LENGTH: 13
<212> TYPE: PRT
<213> ORGANISM: Homo sapiens

<400> SEQUENCE: 62

Met Ser Ser Asp Leu Glu Arg Asp His Arg Pro His Val
1               5                   10

<210> SEQ ID NO 63
<211> LENGTH: 13
<212> TYPE: PRT
<213> ORGANISM: Homo sapiens

<400> SEQUENCE: 63

Ser Asp Leu Glu Arg Asp His Arg Pro His Val Ser Met
1               5                   10

<210> SEQ ID NO 64
<211> LENGTH: 13

<212> TYPE: PRT
<213> ORGANISM: Homo sapiens

<400> SEQUENCE: 64

Leu Glu Arg Asp His Arg Pro His Val Ser Met Pro Gln
1               5                   10

<210> SEQ ID NO 65
<211> LENGTH: 13
<212> TYPE: PRT
<213> ORGANISM: Homo sapiens

<400> SEQUENCE: 65

Arg Asp His Arg Pro His Val Ser Met Pro Gln Asn Ala
1               5                   10

<210> SEQ ID NO 66
<211> LENGTH: 13
<212> TYPE: PRT
<213> ORGANISM: Homo sapiens

<400> SEQUENCE: 66

Asp His Arg Pro His Val Ser Met Pro Gln Asn Ala Asn
1               5                   10

<210> SEQ ID NO 67
<211> LENGTH: 20
<212> TYPE: PRT
<213> ORGANISM: Homo sapiens

<400> SEQUENCE: 67

Ala Pro Phe Arg Ser Ala Leu Glu Ser Ser Pro Ala Asp Pro Ala Thr
1               5                   10                  15

Leu Ser Glu Asp
            20

<210> SEQ ID NO 68
<211> LENGTH: 20
<212> TYPE: PRT
<213> ORGANISM: Homo sapiens

<400> SEQUENCE: 68

Ala Leu Glu Ser Ser Pro Ala Asp Pro Ala Thr Leu Ser Glu Asp Glu
1               5                   10                  15

Ala Arg Leu Leu
            20

<210> SEQ ID NO 69
<211> LENGTH: 20
<212> TYPE: PRT
<213> ORGANISM: Homo sapiens

<400> SEQUENCE: 69

Pro Ala Asp Pro Ala Thr Leu Ser Glu Asp Glu Ala Arg Leu Leu Leu
1               5                   10                  15

Ala Ala Leu Val
            20

<210> SEQ ID NO 70
<211> LENGTH: 20
<212> TYPE: PRT
<213> ORGANISM: Homo sapiens

<400> SEQUENCE: 70

Thr Leu Ser Glu Asp Glu Ala Arg Leu Leu Ala Ala Leu Val Gln
1               5                   10                  15

Asp Tyr Val Gln
            20

<210> SEQ ID NO 71
<211> LENGTH: 20
<212> TYPE: PRT
<213> ORGANISM: Homo sapiens

<400> SEQUENCE: 71

Glu Ala Arg Leu Leu Ala Ala Leu Val Gln Asp Tyr Val Gln Met
1               5                   10                  15

Lys Ala Ser Glu
            20

<210> SEQ ID NO 72
<211> LENGTH: 20
<212> TYPE: PRT
<213> ORGANISM: Homo sapiens

<400> SEQUENCE: 72

Leu Ala Ala Leu Val Gln Asp Tyr Val Gln Met Lys Ala Ser Glu Leu
1               5                   10                  15

Glu Gln Glu Gln
            20

<210> SEQ ID NO 73
<211> LENGTH: 20
<212> TYPE: PRT
<213> ORGANISM: Homo sapiens

<400> SEQUENCE: 73

Gln Asp Tyr Val Gln Met Lys Ala Ser Glu Leu Glu Gln Glu Gln Glu
1               5                   10                  15

Arg Glu Gly Ser
            20

<210> SEQ ID NO 74
<211> LENGTH: 20
<212> TYPE: PRT
<213> ORGANISM: Homo sapiens

<400> SEQUENCE: 74

Met Lys Ala Ser Glu Leu Glu Gln Glu Gln Arg Glu Gly Ser Ser
1               5                   10                  15

Leu Asp Ser Pro
            20

<210> SEQ ID NO 75
<211> LENGTH: 20
<212> TYPE: PRT
<213> ORGANISM: Homo sapiens

<400> SEQUENCE: 75

Leu Glu Gln Glu Gln Glu Arg Glu Gly Ser Ser Leu Asp Ser Pro Arg
1               5                   10                  15

Ser Lys Arg Cys
            20

<210> SEQ ID NO 76

```
<211> LENGTH: 20
<212> TYPE: PRT
<213> ORGANISM: Homo sapiens

<400> SEQUENCE: 76

Glu Arg Glu Gly Ser Ser Leu Asp Ser Pro Arg Ser Lys Arg Cys Gly
1               5                   10                  15

Asn Leu Ser Thr
            20

<210> SEQ ID NO 77
<211> LENGTH: 20
<212> TYPE: PRT
<213> ORGANISM: Homo sapiens

<400> SEQUENCE: 77

Ser Leu Asp Ser Pro Arg Ser Lys Arg Cys Gly Asn Leu Ser Thr Cys
1               5                   10                  15

Met Leu Gly Thr
            20

<210> SEQ ID NO 78
<211> LENGTH: 20
<212> TYPE: PRT
<213> ORGANISM: Homo sapiens

<400> SEQUENCE: 78

Arg Ser Lys Arg Cys Gly Asn Leu Ser Thr Cys Met Leu Gly Thr Tyr
1               5                   10                  15

Thr Gln Asp Phe
            20

<210> SEQ ID NO 79
<211> LENGTH: 20
<212> TYPE: PRT
<213> ORGANISM: Homo sapiens

<400> SEQUENCE: 79

Gly Asn Leu Ser Thr Cys Met Leu Gly Thr Tyr Thr Gln Asp Phe Asn
1               5                   10                  15

Lys Phe His Thr
            20

<210> SEQ ID NO 80
<211> LENGTH: 20
<212> TYPE: PRT
<213> ORGANISM: Homo sapiens

<400> SEQUENCE: 80

Cys Met Leu Gly Thr Tyr Thr Gln Asp Phe Asn Lys Phe His Thr Phe
1               5                   10                  15

Pro Gln Thr Ala
            20

<210> SEQ ID NO 81
<211> LENGTH: 20
<212> TYPE: PRT
<213> ORGANISM: Homo sapiens

<400> SEQUENCE: 81

Tyr Thr Gln Asp Phe Asn Lys Phe His Thr Phe Pro Gln Thr Ala Ile
1               5                   10                  15
```

```
Gly Val Gly Ala
        20

<210> SEQ ID NO 82
<211> LENGTH: 20
<212> TYPE: PRT
<213> ORGANISM: Homo sapiens

<400> SEQUENCE: 82

Asn Lys Phe His Thr Phe Pro Gln Thr Ala Ile Gly Val Gly Ala Pro
1               5                   10                  15

Gly Lys Lys Arg
        20

<210> SEQ ID NO 83
<211> LENGTH: 20
<212> TYPE: PRT
<213> ORGANISM: Homo sapiens

<400> SEQUENCE: 83

Phe Pro Gln Thr Ala Ile Gly Val Gly Ala Pro Gly Lys Lys Arg Asp
1               5                   10                  15

Met Ser Ser Asp
        20

<210> SEQ ID NO 84
<211> LENGTH: 20
<212> TYPE: PRT
<213> ORGANISM: Homo sapiens

<400> SEQUENCE: 84

Ile Gly Val Gly Ala Pro Gly Lys Lys Arg Asp Met Ser Ser Asp Leu
1               5                   10                  15

Glu Arg Asp His
        20

<210> SEQ ID NO 85
<211> LENGTH: 20
<212> TYPE: PRT
<213> ORGANISM: Homo sapiens

<400> SEQUENCE: 85

Pro Gly Lys Lys Arg Asp Met Ser Ser Asp Leu Glu Arg Asp His Arg
1               5                   10                  15

Pro His Val Ser
        20

<210> SEQ ID NO 86
<211> LENGTH: 20
<212> TYPE: PRT
<213> ORGANISM: Homo sapiens

<400> SEQUENCE: 86

Asp Met Ser Ser Asp Leu Glu Arg Asp His Arg Pro His Val Ser Met
1               5                   10                  15

Pro Gln Asn Ala
        20

<210> SEQ ID NO 87
<211> LENGTH: 20
<212> TYPE: PRT
<213> ORGANISM: Homo sapiens
```

```
<400> SEQUENCE: 87

Met Ser Ser Asp Leu Glu Arg Asp His Arg Pro His Val Ser Met Pro
1               5                   10                  15

Gln Asn Ala Asn
            20
```